United States Patent
Kuo

(10) Patent No.: US 11,436,191 B2
(45) Date of Patent: Sep. 6, 2022

(54) SYSTEMS AND METHODS FOR ANONYMIZING PATENT IMAGES IN RELATION TO A CLINICAL DATA FILE

(71) Applicant: Align Technology, Inc., San Jose, CA (US)

(72) Inventor: Eric E. Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 84 days.

(21) Appl. No.: 16/270,891

(22) Filed: Feb. 8, 2019

(65) Prior Publication Data
US 2019/0171618 A1 Jun. 6, 2019

Related U.S. Application Data

(63) Continuation of application No. 14/272,186, filed on May 7, 2014, now abandoned, which is a continuation
(Continued)

(51) Int. Cl.
*G06F 16/16* (2019.01)
*G06Q 10/10* (2012.01)
(Continued)

(52) U.S. Cl.
CPC ............ *G06F 16/16* (2019.01); *G06Q 10/10* (2013.01); *G16H 10/60* (2018.01); *G16H 30/20* (2018.01)

(58) Field of Classification Search
CPC .............................. G16H 10/60; G16H 30/20
See application file for complete search history.

(56) References Cited

U.S. PATENT DOCUMENTS 2,171,695 A 9/1939 Harper
2,194,790 A 3/1940 Gluck
(Continued)

FOREIGN PATENT DOCUMENTS

AU 517102 B 11/1977
AU 3031677 A 11/1977
(Continued)

OTHER PUBLICATIONS

Blanquer, Ignacio et al. "A peer-to-peer environment to share medical images and diagnoses providing context-based searching." 13th Euromicro Conference on Parallel, Distributed and Network-Based Processing (2005): 42-48 (Year: 2005).*
(Continued)

*Primary Examiner* — Sheetal R Paulson
(74) *Attorney, Agent, or Firm* — Shay Glenn LLP

(57) ABSTRACT

Personal data file embodiments and methods for creating the same are provided. In some embodiments, the methods include obtaining an original patient data file including patient medical information comprising one or more patient images; receiving first instructions to designate only a portion of the one or more patient images in the original patient data file as private; providing a privacy region over the at least a portion of the one or more patient images; creating one or more anonymized patient images; displaying the one or more anonymized patient images alongside at least a part of the patient personal information in a display; receiving a first input for a first modification to the one or more anonymized patient images related to implementation of the treatment plan; associating the first modification with the patient personal; and displaying the first modification as a first layer on the one or more anonymized patient images.

25 Claims, 4 Drawing Sheets

Related U.S. Application Data of application No. 11/983,280, filed on Nov. 8, 2007, now Pat. No. 8,738,394.

(51) Int. Cl.
  *G16H 10/60* (2018.01)
  *G16H 30/20* (2018.01)

(56) References Cited

U.S. PATENT DOCUMENTS

| | | |
|---|---|---|
| 2,467,432 A | 4/1949 | Kesling |
| 2,531,222 A | 11/1950 | Kesling |
| 2,835,628 A | 5/1958 | Saffir |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,503,127 A | 3/1970 | Kasdin et al. |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,813,781 A | 6/1974 | Forgione |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,039,653 A | 8/1977 | DeFoney et al. |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,278,087 A | 7/1981 | Theeuwes |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,450,150 A | 5/1984 | Sidman |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,741,700 A | 5/1988 | Barabe |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,818,542 A | 4/1989 | De Luca et al. |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,968,251 A | 11/1990 | Darnell |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,049,077 A | 9/1991 | Goldin et al. |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |

(56) References Cited

U.S. PATENT DOCUMENTS

| | | |
|---|---|---|
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,911,576 A | 6/1999 | Ulrich et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 5,993,413 A | 11/1999 | Aaltonen et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmel et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |

(56) References Cited

U.S. PATENT DOCUMENTS

| | | |
|---|---|---|
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Wood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,194,781 B1 | 3/2007 | Orjela |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Blester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |

(56) References Cited

U.S. PATENT DOCUMENTS

| | | |
|---|---|---|
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,841,464 B2 | 11/2010 | Cinader et al. |
| 7,854,609 B2 | 12/2010 | Chen et al. |
| 7,860,342 B2 * | 12/2010 | Levien ............... G06F 21/6254 358/1.14 |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,075,306 B2 | 12/2011 | Kitching et al. |
| 8,077,949 B2 | 12/2011 | Liang et al. |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,126,025 B2 | 2/2012 | Takeda |
| 8,136,529 B2 | 3/2012 | Kelly |
| 8,144,954 B2 | 3/2012 | Quadling et al. |
| 8,152,518 B2 | 4/2012 | Kuo |
| 8,172,569 B2 | 5/2012 | Matty et al. |
| 8,197,252 B1 | 6/2012 | Harrison |
| 8,201,560 B2 | 6/2012 | Dembro |
| 8,275,180 B2 | 9/2012 | Kuo |
| 8,292,617 B2 | 10/2012 | Brandt et al. |
| 8,294,657 B2 | 10/2012 | Kim et al. |
| 8,296,952 B2 | 10/2012 | Greenberg |
| 8,306,608 B2 | 11/2012 | Mandelis et al. |
| 8,314,764 B2 | 11/2012 | Kim et al. |
| 8,332,015 B2 | 12/2012 | Ertl |
| 8,401,826 B2 | 3/2013 | Cheng et al. |
| 8,465,280 B2 | 6/2013 | Sachdeva et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,639,477 B2 | 1/2014 | Chelnokov et al. |
| 8,650,586 B2 | 2/2014 | Lee et al. |
| 8,738,394 B2 | 5/2014 | Kuo |
| 8,771,149 B2 | 7/2014 | Rahman et al. |
| 8,843,381 B2 | 9/2014 | Kuo et al. |
| 8,870,566 B2 | 10/2014 | Bergersen |
| 8,874,452 B2 | 10/2014 | Kuo |
| 8,899,976 B2 | 12/2014 | Chen et al. |
| 8,944,812 B2 | 2/2015 | Kou |
| 8,992,216 B2 | 3/2015 | Karazivan |
| 9,004,915 B2 | 4/2015 | Moss et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,277,972 B2 | 3/2016 | Brandt et al. |
| 9,403,238 B2 | 8/2016 | Culp |
| 9,414,897 B2 | 8/2016 | Wu et al. |
| 9,463,287 B1 | 10/2016 | Lorberbaum et al. |
| 9,492,243 B2 | 11/2016 | Kuo |
| 9,566,132 B2 | 2/2017 | Stone-Collonge et al. |
| 9,589,329 B2 | 3/2017 | Levin |
| 9,675,427 B2 | 6/2017 | Kopelman |
| 9,730,769 B2 | 8/2017 | Chen et al. |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 2001/0002310 A1 | 5/2001 | Chishti et al. |
| 2001/0032100 A1 * | 10/2001 | Mahmud ............... G06Q 50/22 705/2 |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |

(56) References Cited

U.S. PATENT DOCUMENTS

| | | |
|---|---|---|
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0008259 A1 | 1/2003 | Kuo et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0211440 A1 | 11/2003 | Kuo et al. |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1* | 6/2005 | Ramamurthy ......... G06N 5/022 706/45 |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0125256 A1* | 9/2005 | Schoenberg et al. ... G06F 19/00 705/2 |
| 2005/0216314 A1* | 9/2005 | Secor .................... G16H 10/60 705/3 |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115782 A1 | 6/2006 | Li et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fomoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Belski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1* | 8/2007 | Ombrellaro ............ G06Q 10/10 600/300 |
| 2007/0199929 A1 | 8/2007 | Rippl et al. |
| 2007/0207434 A1 | 9/2007 | Kuo et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |

(56) References Cited

U.S. PATENT DOCUMENTS

| | | |
|---|---|---|
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1* | 3/2008 | Park ............... G06Q 10/10 705/3 |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0136890 A1 | 5/2009 | Kang et al. |
| 2009/0181346 A1 | 7/2009 | Orth |
| 2009/0210032 A1 | 8/2009 | Beiski et al. |
| 2009/0218514 A1 | 9/2009 | Klunder et al. |
| 2009/0286195 A1 | 11/2009 | Sears et al. |
| 2009/0298017 A1 | 12/2009 | Boerjes et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0145664 A1 | 6/2010 | Hultgren et al. |
| 2010/0145898 A1 | 6/2010 | Malfliet et al. |
| 2010/0165275 A1 | 7/2010 | Tsukamoto et al. |
| 2010/0179789 A1 | 7/2010 | Sachdeva et al. |
| 2010/0196837 A1 | 8/2010 | Farrell |
| 2010/0217130 A1 | 8/2010 | Weinlaender |
| 2010/0231577 A1 | 9/2010 | Kim et al. |
| 2010/0281370 A1 | 11/2010 | Rohaly et al. |
| 2011/0104630 A1 | 5/2011 | Matov et al. |
| 2012/0166213 A1 | 6/2012 | Arnone et al. |
| 2013/0103176 A1 | 4/2013 | Kopelman et al. |
| 2014/0136222 A1 | 5/2014 | Arnone et al. |
| 2014/0142902 A1 | 5/2014 | Chelnokov et al. |
| 2014/0280376 A1 | 9/2014 | Kuo |
| 2015/0004553 A1 | 1/2015 | Li et al. |
| 2015/0132708 A1 | 5/2015 | Kuo |
| 2015/0173856 A1 | 6/2015 | Iowe et al. |
| 2015/0238283 A1 | 8/2015 | Tanugula et al. |
| 2015/0320320 A1 | 11/2015 | Kopelman et al. |
| 2015/0320532 A1 | 11/2015 | Matty et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0302885 A1 | 10/2016 | Matov et al. |
| 2016/0338799 A1 | 11/2016 | Wu et al. |
| 2016/0367339 A1 | 12/2016 | Khardekar et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0071705 A1 | 3/2017 | Kuo |
| 2017/0100212 A1 | 4/2017 | Sherwood et al. |
| 2017/0100213 A1 | 4/2017 | Kuo |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0258555 A1 | 9/2017 | Kopelman |
| 2017/0319296 A1 | 11/2017 | Webber et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071055 A1 | 3/2018 | Kuo |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0228359 A1 | 8/2018 | Meyer et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0125494 A1 | 5/2019 | Li et al. |
| 2019/0183614 A1 | 6/2019 | Levin |

FOREIGN PATENT DOCUMENTS

| | | | |
|---|---|---|---|
| CA | 1121955 | A1 | 4/1982 |
| CN | 1655732 | A | 8/2005 |
| CN | 1655733 | A | 8/2005 |
| CN | 1867317 | A | 11/2006 |
| DE | 2749802 | A1 | 5/1978 |
| DE | 3526198 | A1 | 2/1986 |
| DE | 4207169 | A1 | 9/1993 |
| DE | 69327661 | T2 | 7/2000 |
| DE | 102005043627 | A1 | 3/2007 |
| EP | 0428152 | A1 | 5/1991 |
| EP | 490848 | A2 | 6/1992 |
| EP | 541500 | A1 | 5/1993 |
| EP | 714632 | B1 | 5/1997 |
| EP | 774933 | B1 | 12/2000 |
| EP | 731673 | B1 | 5/2001 |
| EP | 1941843 | A2 | 7/2008 |
| EP | 1989764 | B1 | 7/2012 |
| ES | 463897 | A1 | 1/1980 |
| FR | 2369828 | A1 | 6/1978 |
| FR | 2867377 | A1 | 9/2005 |
| GB | 1550777 | A | 8/1979 |

(56) References Cited

FOREIGN PATENT DOCUMENTS

| | | | |
|---|---|---|---|
| JP | 53-058191 A | 5/1978 | |
| JP | 04-028359 A | 1/1992 | |
| JP | 08-508174 A | 9/1996 | |
| JP | 09-19443 A | 1/1997 | |
| JP | 2003245289 A | 9/2003 | |
| JP | 2000339468 A | 9/2004 | |
| JP | 2005527320 A | 9/2005 | |
| JP | 2005527321 A | 9/2005 | |
| JP | 2006043121 A | 2/2006 | |
| JP | 2007151614 A | 6/2007 | |
| JP | 2007260158 A | 10/2007 | |
| JP | 2007537824 A | 12/2007 | |
| JP | 2008067732 A | 3/2008 | |
| JP | 2008523370 A | 7/2008 | |
| JP | 2009000412 A | 1/2009 | |
| JP | 2009018173 A | 1/2009 | |
| JP | 2009078133 A | 4/2009 | |
| JP | 2009101386 A | 5/2009 | |
| KR | 10-20020062793 A | 7/2002 | |
| KR | 10-20070108019 A | 11/2007 | |
| TW | 480166 B | 3/2002 | |
| WO | WO91/004713 A1 | 4/1991 | |
| WO | WO92/03102 A1 | 3/1992 | |
| WO | WO94/010935 A1 | 5/1994 | |
| WO | WO96/23452 A1 | 8/1996 | |
| WO | WO98/032394 A1 | 7/1998 | |
| WO | WO-9829790 A2 * | 7/1998 | ........... G06F 19/322 |
| WO | WO98/044865 A1 | 10/1998 | |
| WO | WO01/08592 A1 | 2/2001 | |
| WO | WO01/85047 A2 | 11/2001 | |
| WO | WO02/017776 A2 | 3/2002 | |
| WO | WO02/024100 A1 | 3/2002 | |
| WO | WO02/058583 A1 | 8/2002 | |
| WO | WO02/062252 A1 | 8/2002 | |
| WO | WO02/095475 A1 | 11/2002 | |
| WO | WO03/003932 A2 | 1/2003 | |
| WO | WO2005/114183 A1 | 12/2005 | |
| WO | WO2006/096558 A2 | 9/2006 | |
| WO | WO2006/100700 A1 | 9/2006 | |
| WO | WO2006/133548 A1 | 12/2006 | |
| WO | WO2007/019709 A2 | 2/2007 | |
| WO | WO2007/071341 A1 | 6/2007 | |
| WO | WO2007/103377 A2 | 9/2007 | |
| WO | WO2008/115654 A1 | 9/2008 | |
| WO | WO2009/016645 A2 | 2/2009 | |

OTHER PUBLICATIONS

Dental Monitoring; Basics: How to put the cheek retractor?; 1 page (Screenshot); retrieved from the interenet (https://www.youtube.com/watch?v=6K1HXw4Kq3c); May 27, 2016.

Dental Monitoring; Dental monitoring tutorial; 1 page (Screenshot); retrieved from the internet (https:www.youtube.com/watch?v=Dbe3udOf9_c); Mar. 18, 2015.

Ecligner Selfie; Change your smile; 1 page (screenshot); retrieved from the internet (https:play.google.com/store/apps/details?id=parklict.ecligner); on Feb. 13, 2018.

Lawrence; Salivary markers of systemic disease: noninvasive diagnosis of disease and monitoring of general health; Journal of the Canadian Dental Association Clinical Practice; 68(3); pp. 170-174; Mar. 2002.

Nishanian et al.; Oral fluids as an alternative to serum for measurement of markers of immune activation; Clinical and Diagnostic Laboratory Immunology; 5(4); pp. 507-512; Jul. 1998.

Svec et al.; Molded rigid monolithic porous polymers: an inexpensive, efficient, and versatile alternative to beads for design of materials for numerous applications; Industrial and Engineering Chemistry Research; 38(1); pp. 34-48; Jan. 4, 1999.

U.S. Food and Drug Administration; Color additives; 3 pages; retrieved from the internet (https://websrchive.org/web/20070502213911/http://www.cfsan.fda.gov/~dms/col.toc.html); last known as May 2, 2007.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et al; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Bartels et al.; An Introduction to Splines for Use in Computer Graphics and Geometric Modeling; Morgan Kaufmann Publishers; pp. 422-425 Jan. 1, 1987.

(56) References Cited

OTHER PUBLICATIONS

Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Begole et al.; A Computer System for the Analysis of Dental Casts; The Angle Orthodontist; 51(3); pp. 252-258; Jul. 1981.
Berland; The use of smile libraries for cosmetic dentistry; Dental Tribune: Asia Pacific Edition; pp. 16-18; Mar. 29, 2006.
Bernabe et al; Are the lower incisors the best predictors for the unerupted canine and premolars sums? An analysis of Peruvian sample; The Angle Orthodontist; 75(2); pp. 202-207; Mar. 2005.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bookstein; Principal warps: Thin-plate splines and decomposition of deformations; IEEE Transactions on pattern analysis and machine intelligence; 11(6); pp. 567-585; Jun. 1989.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cadent Inc.; OrthoCAD ABO user guide; 38 pages; Dec. 21, 2005.
Cadent Inc.; Reviewing and modifying an orthoCAD case; 4 pages; Feb. 14, 2005.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Collins English Dictionary; Teeth (definition); 9 pages; retrieved from the internet (https:www.collinsdictionary.com/us/dictionary/english/teeth) on May 13, 2019.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cuttng et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
Daniels et al.; The development of the index of complexity outcome and need (ICON); British Journal of Orthodontics; 27(2); pp. 149-162; Jun. 2000.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dentrix; Dentrix G3, new features; 2 pages; retrieved from the internet (http://www.dentrix.com/g3/new_features/index.asp); on Jun. 6, 2008.
Dent-x; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Giacomo et al.; Clinical application of sterolithographic surgical guides for implant placement: Preliminary results; Journal Periodontolgy; 76(4); pp. 503-507; Apr. 2005.

(56) References Cited

OTHER PUBLICATIONS

Di Muzio et al.; Minimum intensity projection (MinIP); 6 pages; retrieved from the internet (https://radiopaedia.org/articles/minimum-intensity-projection-minip) on Sep. 6, 2018.

DICOM to surgical guides; (Screenshot)1 page; retrieved from the internet at YouTube (https://youtu.be/47KtOmCEFQk); Published Apr. 4, 2016.

dictionary.com; Plural (definition); 6 pages; retrieved from the internet ( https://www.dictionary.eom/browse/plural#) on May 13, 2019.

dictionary.com; Quadrant (definition); 6 pages; retrieved from the internet ( https://www.dictionary.com/browse/quadrant?s=t) on May 13, 2019.

Doruk et al.; The role of the headgear timer in extraoral co-operation; European Journal of Orthodontics; 26; pp. 289-291; Jun. 1, 2004.

Doyle; Digital Dentistry; Computer Graphics World; pp. 50-52 andp. 54; Oct. 2000.

Duret et al.; CAD/CAM Imaging in Dentistry; Current Opinion in Dentistry; 1(2); pp. 150-154; Apr. 1991.

Duret et al.; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment-concept and analysis of accuracy; J. Biomech.; 32(1); pp. 81-85; (Abstract Only) Jan. 1999.

Futterling et al.; Automated Finite Element Modeling of a Human Mandible with Dental Implants; JS WSCG '98—Conference Program; 8 pages; retrieved from the Internet (https://dspace5.zcu.ez/bitstream/11025/15851/1 /Strasser_98.pdf); on Aug. 21, 2018.

Gansky; Dental data mining: potential pitfalls and practical issues; Advances in Dental Research; 17(1); pp. 109-114; Dec. 2003.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Geomagic; Dental reconstruction; 1 page; retrieved from the internet (http://geomagic.com/en/solutions/industry/detal_desc.php) on Jun. 6, 2008.

Gim-alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Gottschalk et al.; OBBTree: A hierarchical structure for rapid interference detection; 12 pages; (http://www.cs.unc.edu/?geom/ OBB/OBBT.html); relieved from te internet (https://www.cse.iitk.ac.in/users/amit/courses/RMP/presentations/dslamba/presentation/sig96.pdf) on Apr. 25, 2019.

gpsdentaire.com; Get a realistic smile simulation in 4 steps with GPS; a smile management software; 10 pages; retrieved from the internet (http://www.gpsdentaire.com/en/preview/) on Jun. 6, 2008.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

Invisalign; You were made to move. There's never been a better time to straighten your teeth with the most advanced clear aligner in the world; Product webpage; 2 pages; retrieved from the internet (www.invisalign.com/) on Dec. 28, 2017.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Karaman et al.; A practical method of fabricating a lingual retainer; Am. Journal of Orthodontic and Dentofacial Orthopedics; 124(3); pp. 327-330; Sep. 2003.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

(56) References Cited

OTHER PUBLICATIONS

Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
Mantzikos et al.; Case report: Forced eruption and implant site development; The Angle Orthodontist; 68(2); pp. 179-186; Apr. 1998.
Martinelli et al.; Prediction of lower permanent canine and premolars width by correlation methods; The Angle Orthodontist; 75(5); pp. 805-808; Sep. 2005.
McCann; Inside the Ada; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Methot; Get the picture with a gps for smile design in 3 steps; Spectrum; 5(4); pp. 100-105; (year of pub. sufficiently earlier than effective US filing date and any foreign priority date) 2006.
Moermann et al., Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy as One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Newcombe; DTAM: Dense tracking and mapping in real-time; 8 pages; retrieved from the internet (http://www.doc.ic.ac.uk/2ajd/Publications/newcombe_etal_iccv2011.pdf; on Dec. 2011.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Nourallah et al.; New regression equations for prediciting the size of unerupted canines and premolars in a contemporary population; The Angle Orthodontist; 72(3); pp. 216-221; Jun. 2002.
Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.
ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Paredes et al.; A new, accurate and fast digital method to predict unerupted tooth size; The Angle Orthodontist; 76(1); pp. 14-19; Jan. 2006.
Patterson Dental; Cosmetic imaging; 2 pages retrieved from the internet (http://patterson.eaglesoft.net/cnt_di_cosimg.html) on Jun. 6, 2008.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree ESSIX & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.

(56) References Cited

OTHER PUBLICATIONS

Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Sarment et al.; Accuracy of implant placement with a sterolithographic surgical guide; journal of Oral and Maxillofacial Implants; 118(4); pp. 571-577; Jul. 2003.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al.; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cosjmaging.php) on Jun. 6, 2008.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
The American Heritage, Stedman's Medical Dictionary; Gingiva; 3 pages; retrieved from the interent (http://reference.com/search/search?q=gingiva) on Nov. 5, 2004.

Thera Mon; "Microsensor"; 2 pages; retrieved from the internet (www.english.thera-mon.com/the-product/transponder/index.html); on Sep. 19, 2016.
THORLABS; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Varady et al.; Reverse Engineering of Geometric Models' An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Vevin et al.; Pose estimation of teeth through crown-shape matching; In Medical Imaging; Image Processing of International Society of Optics and Photonics; vol. 4684; pp. 955-965; May 9, 2002.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Watson et al.; Pressures recorded at te denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxillofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

(56) References Cited

OTHER PUBLICATIONS

Wolf; Three-dimensional structure determination of semi-transparent objects from holographic data; Optics Communications; 1(4); pp. 153-156; Sep. 1969.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Kong Dental Journal; 3(2); pp. 107-115; Dec. 2006.
WSCG'98 —Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yaltara Software; Visual planner; 1 page; retrieved from the internet (http://yaltara.com/vp/) on Jun. 6, 2008.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Zhang et al.; Visual speech features extraction for improved speech recognition; 2002 IEEE International conference on Acoustics, Speech and Signal Processing; vol. 2; 4 pages; May 13-17, 2002.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." filed Dec. 24, 2018.
Kopleman et al., U.S. Appl. No. 16/220,381 entitled "Closed loop adaptive orthodontic treatment methods and apparatuses," filed Dec. 14, 2018.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Virtual Orthodontics, "Our Innovative Software," http://www.virtualorthodontics.com/innovativesoftware.html, 2005, 3 pp.

* cited by examiner

SYSTEMS AND METHODS FOR ANONYMIZING PATENT IMAGES IN RELATION TO A CLINICAL DATA FILE

PRIORITY INFORMATION

This application is a Continuation of U.S. application Ser. No. 14/272,186, filed May 7, 2014, titled "PERSONAL DATA FILE," now U.S. patent application Publication No. 2014-0280376, which is a Continuation of U.S. patent application Ser. No. 11/983,280, filed Nov. 8, 2007, titled "CLINICAL DATA FILE," now U.S. Pat. No. 8,738,394, the specification of which is incorporated herein by reference.

BACKGROUND

The present disclosure relates to devices, files, mediums, and methods for keeping medical information private. The present disclosure, for example, includes a data file, where a treatment professional can designate as private, at least a portion of the medical or other information therein.

In some instances, it is beneficial when planning an orthodontic treatment process to confer and discuss various possible treatment routes with other treatment professionals (e.g., specialists such as orthodontists, oral surgeons, periodontists, and/or general dentists). However, although patient data can now be sent almost instantaneously over the Internet, it can be desirable to keep patient medical information as well as treatment professional information private (e.g., hidden) from a conferring treatment professional.

In addition, in determining a treatment process, information can be gathered in many different file formats. For example, information can include two and/or three-dimensional images, digital and/or analog images, and/or digital and/or analog video of a patient's mouth and/or surrounding features. Also, text files can be generated, including notes, comments, prescription notes, and/or medical history. However, difficulties can arise in viewing and sending multiple types of files since each type of file may require that each treatment professional have special software for each type of file.

DETAILED DESCRIPTION

According to the present disclosure, systems, devices, files, and methods are provided for converting clinical data to a single format and creating a clinical data file including the clinical data in the single format. Also, in some embodiments, treatment professional information, patient personal information, and/or patient images designated as private included in the clinical data file can be provided upon entering a pass code. As used herein, "clinical data" refers to data generated in the process of treating a patient. For example, clinical data can include, but is not limited to, patient medical information (e.g., dental or other medical information) items including x-rays, two and/or three-dimensional (3-D) models of a medical patient's mouth, and/or digital and/or analog pictures of the patient's teeth. In addition, clinical data can include prescription notes and/or treatment professional comments.

Clinical data can also include other information generated when forming a treatment plan for the patient. For example, such other information can include information that is generated in instances where the treatment plan is to reposition the patient's teeth with a number of stages of incrementally moving teeth using a plurality of discrete appliances, where each appliance successively moves one or more of the patient's teeth by incremental amounts.

In some embodiments, methods of the present disclosure can be carried out by instructions stored in memory and executed by a processor in a computing device. The instructions can, for example, be included in a computing device readable medium. In such embodiments, a computing device readable medium can be any medium that can store computing device readable information thereon. Suitable examples include optically or magnetically readable forms of media, among others.

Figure 1:
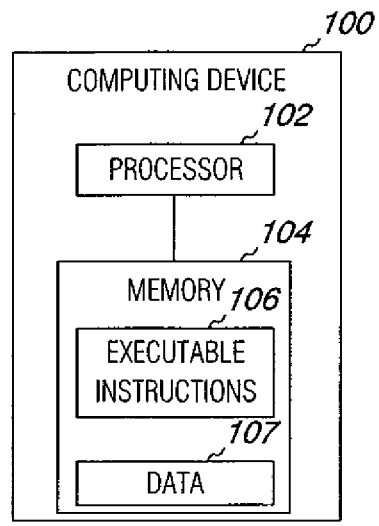
FIG. 1 illustrates a computing device embodiment to perform the methods of the present disclosure.

FIG. 1 illustrates a computing device embodiment to perform the methods of the present disclosure. In some embodiments, the computing device 100 can be used to create a clinical data file. In the computing device embodiment of FIG. 1, the device 100 includes one or more processors 102 in communication with one or more memory locations 104. The memory 104 can include a number of instructions 106 that can be executed on the processor 102. Memory 104 can also include one or more items of data 107 that can be used in the execution of the instructions 106 by the processor 102. The instructions 106 can, for example, be executed by the processor 102 to cause the computing device 100 to perform a method of the present disclosure, as described herein.

Figure 2:
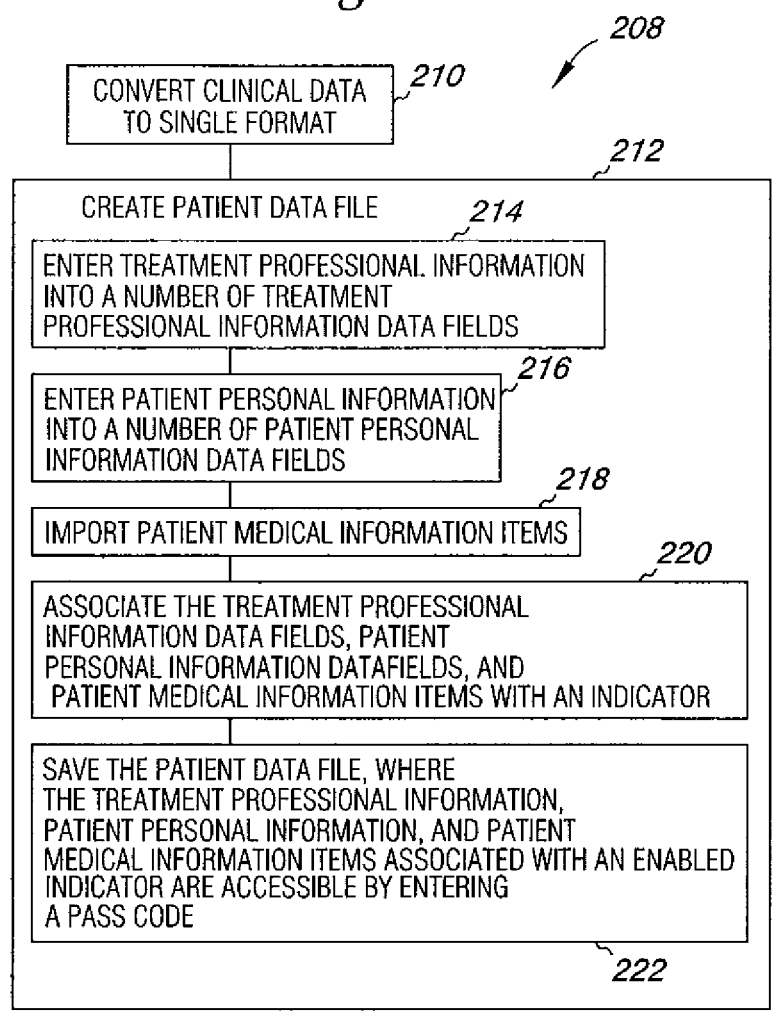
FIG. 2 illustrates a method for creating a clinical data file and securing medical information according to an embodiment of the present disclosure.

FIG. 2 illustrates a method for creating a clinical data file and securing medical information according to embodiments of the present disclosure. Unless explicitly stated, the method embodiments described herein are not constrained to a particular order or sequence. Additionally, some of the described method embodiments or elements thereof can occur or be performed at the same point in time.

As illustrated at block 210, the method 208 includes converting clinical data to a single format. In some embodiments, the conversion of clinical data can include converting all clinical data to a single format that is a different format than the clinical data is created in originally. For example, in some embodiments, the clinical data can be converted into a portable document format (PDF). In some embodiments, the conversion of clinical data can include converting a portion of the clinical data to a single format, where some clinical data is currently in the single format.

As illustrated at block 212, the method 208 includes creating a clinical data file 212 including the clinical data. As illustrated, creating the clinical data file 212 can include several steps.

For example, at block 214 treatment professional information can be entered into a number of treatment professional information data fields in a treatment professional profile section of the clinical data file. Treatment professional information can include, but is not limited to, treatment professional name, office address, office contact information (e.g., telephone number, fax number, electronic mail address), office logo, treatment professional photograph, practice mission/personal statement, and/or treatment professional resume highlights, among other items.

At block 216, patient personal information can be entered into a number of patient personal information data fields in a patient profile section of the clinical data file. The patient profile section can, for example, include, patient name, address, contact information (e.g., telephone number, fax number, electronic mail address), social security number, date of birth, gender, and/or insurance, among others.

At block 218, patient medical information items (e.g., patient images) can be imported into the clinical data file. In some embodiments, the patient medical information items can include several different types of patient images including x-ray, two or three-dimensional, and/or digital and/or analog images, among others.

In addition, in some instances, the various patient images may be created in many different file formats, making it difficult to view all of the patient images without specific software for each file format. By providing (e.g., converting) the clinical data (e.g., patient image) in a single format, and subsequently importing the patient images into the clinical data file, patient images that may have been created using different software can be viewed from the clinical data file using a single file viewer enabled by a single software application.

The many different types of patient images can include, for example, facial anterior (repose), facial anterior (smiling), profile (repose), profile (smiling), right buccal, left buccal, anterior intraoral, upper occlusal, lower occlusal, close-up smile, individual teeth, patient medical history (e.g., dental history), patient diagnosis, a three-dimensional (3-D) model of the patient's mouth (e.g., ClinCheck 3-D model, Invisalign® proprietary software that illustrates the movement of teeth), full mouth series x-rays, panoramic x-rays, cephalometric x-rays, and/or individual radiographs, among others. Since the patient images can include many different types of images, in some embodiments, creating the clinical data file 212 can include labeling the imported patient images according to data type (e.g., profile (smiling)).

In addition, in some embodiments, creating the clinical data file 212 can include positioning at least one patient image in a data file menu, as discussed further herein. For example, the patient images can be positioned in a hierarchy (e.g., a descending order) of importance according to a treatment professional. In some embodiments, instructions can be executed by the processor to put the imported images into a default position in the data file menu.

In some embodiments, at least one patient image can be represented by a thumbnail on the data file menu. In some such embodiments, instructions can be provided to select a thumbnail of a patient image which can initiate executable instructions to access an enlarged patient image and present the enlarged image on a display, among other functions.

As illustrated at block 220, creating the clinical data file 212 can include associating the treatment professional information data fields, patient personal information data fields, and/or patient medical information items with an indicator. The indicator functionality can be accomplished in various manners. For example, in some embodiments, the indicator can be a box that can be checked to enable the indicator.

In various embodiments, the indicator can be a drop down menu listing possible properties of the data field and/or information item. For example, the drop down menu properties can include, "hide information", "display information", and/or "secure information," among other suitable functions.

In such embodiments, when "hide information" is selected, the information contained in the data field and/or the information item, or portions thereof, can be hidden from a user viewing the clinical data file. When "display information" is selected, the information contained in the data field and/or the information item can be shown to the user viewing the clinical data file. When "secure information" is selected, the information contained in the data field and/or the information item can be shown by entering a pass code.

Also, as illustrated at block 222, the method 208 includes saving the clinical data file, where the treatment professional information, patient personal information, and/or patient medical information items associated with an enabled indicator can be accessed by entering a pass code.

In some embodiments, a method can include instructions executed by the processor to embed a pass code into the clinical data file once the clinical data file is saved in memory. For example, the pass code can be used to restrict viewing of some information (e.g., text/images, time based information, regions of images (e.g., eyes)), some files, and/or restrict transfer and/or modification of such information/files.

The pass code, for example, can be a password known to the user. The pass code can alternatively be an identifier associated with a computing device, such as an identifier uniquely associated with the computing device or network when the clinical data file is saved.

Further, a method can include instructions that are executed by the processor to allow the clinical data file to be modified after the pass code is entered into the computing device. By embedding a pass code into the clinical data file and preventing modifications to the clinical data file without the pass code, the clinical data file can be viewed by a limited number of users, however, only authorized users can modify the clinical data file. In addition, limiting modification ability can help to maintain the authenticity and integrity of the clinical data file.

In some embodiments, multiple pass codes can be used, where one pass code can allow modifications to the clinical data file and a second pass code can allow the ability to view the clinical data file without the ability to modify. Other pass codes can also be created to allow the viewing of specific items and/or areas of the clinical data file.

Once the clinical data file has been created and saved, instructions can be executed by the processor to view the clinical data file on a display. Viewing the clinical data file can include viewing the data file menu, the patient profile, and/or the treatment professional profile, among other things, as discussed herein.

Figure 3:
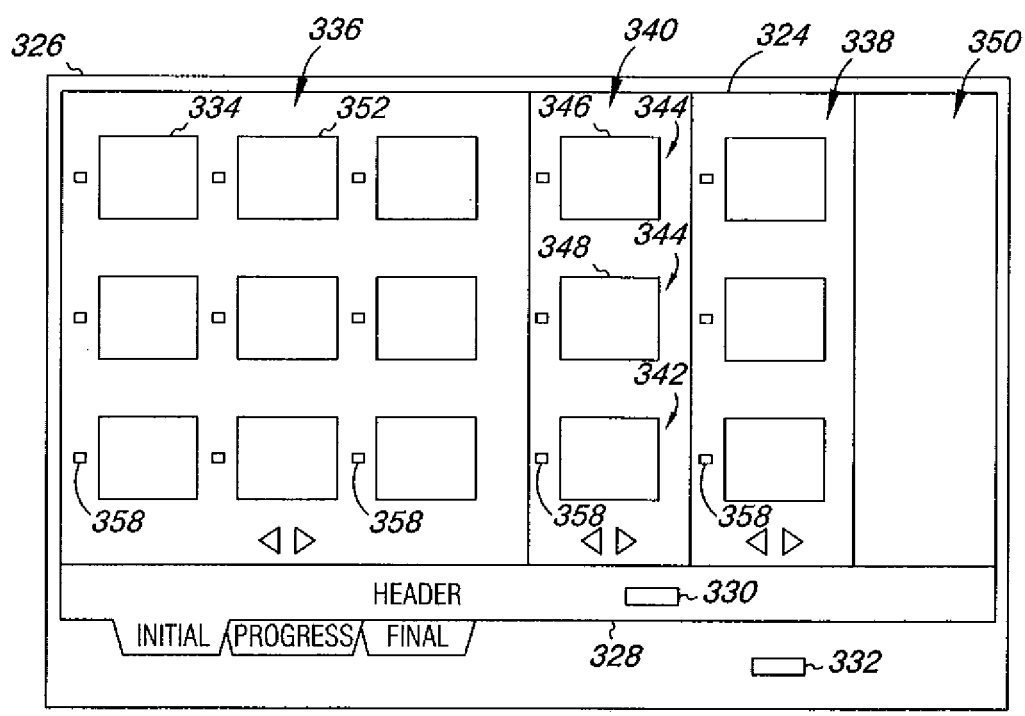
FIG. 3 is an illustration of a data file menu on a display according to an embodiment of the present disclosure.

FIG. 3 is an illustration of a data file menu 324 on a display 326 according to embodiments of the present disclosure. The data file menu 324 can include a header 328 displaying various patient personal information, such as a patient's name and age, among other items. For example, in some embodiments, the header 328 can display a patient's initials to maintain a patient's privacy, as discussed herein.

The header 328 can also include a patient personal information icon 330. When the patient personal information icon 330 is selected, instructions can be executed by the processor to view the patient profile section, as discussed herein.

In addition, the data file menu 324 can include a treatment professional information icon 332. Similarly, when the treatment professional icon 332 is selected, instructions can be executed by the processor to view the treatment professional profile section, as discussed herein.

In some embodiments, the patient images 334 can be separated into sections on the data file menu 324. For example, as shown in FIG. 3, patient images 334 that are photographs can be in a photograph section 336, patient images 334 that are x-rays can be in an x-ray section 338, and a third section 340 can include 3-D models 342 and text information 344.

In some embodiments, the text information 344 can be free text 346. In addition, as discussed herein, patient images 334 can include patient medical history. In some embodiments, the patient medical history can be a text image 348. In addition, in some embodiments, the data file menu 324 can include a comment section 350.

As discussed herein, in some embodiments, at least one patient image 334 can be associated with a thumbnail 352. As shown in FIG. 3, the data file menu 324 can include thumbnails 352 of the patient images 334 so that more images can be seen at one time.

In addition, when the patient image 334 is originally imported into the clinical data file, the patient image 334 and/or thumbnail 352 can be associated with an indicator 358. In some embodiments, the indicator 358 can be a box, as shown in FIG. 3, where the box can be "checked" to enable the indicator 358 when enabled executable instructions can be initiated to perform a function having to do with the image.

In some such embodiments, when an indicator 358 is enabled, instructions executable by the processor can hide the image 334 associated with the enabled indicator 358 when the clinical data file is being viewed by a user, as discussed herein. Therefore, when a user views the clinical data file, the user can see the data file menu 324 as illustrated in FIG. 3, without the indicators 358.

Figure 4:
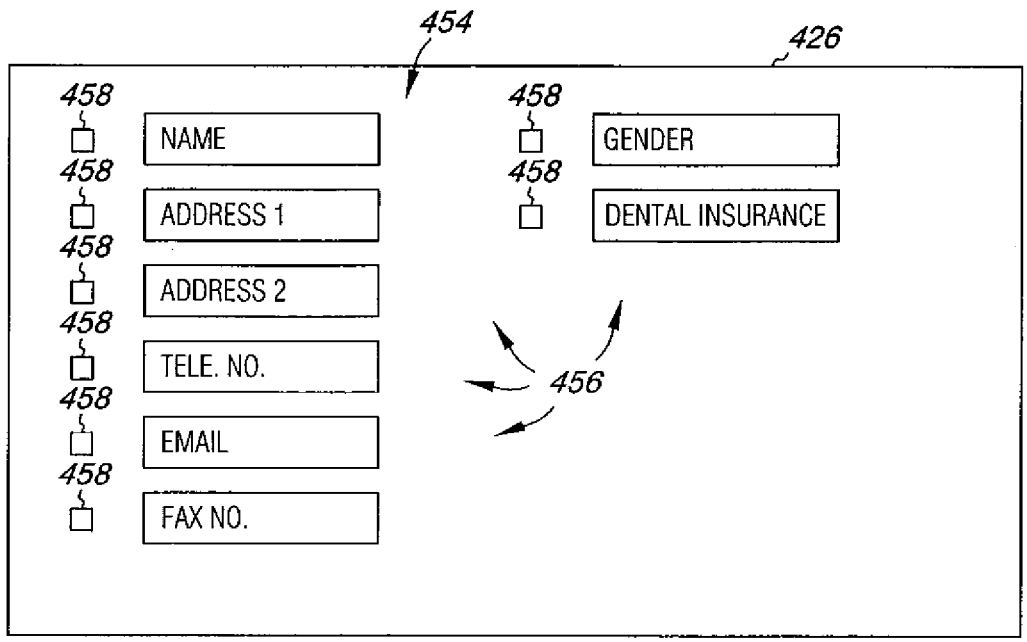
FIG. 4 is an illustration of a display of a patient profile section according to an embodiment of the present disclosure.

FIG. 4 is an illustration of a display 426 of a patient profile section 454 according to embodiments of the present disclosure. The patient profile section 454 illustrated shows the section 454 when the clinical data file is created.

In FIG. 4, the patient profile section 454 can include various data fields 456 that can be filled in with different types of information including, for example, name, address, telephone number, email, fax number, gender, and/or insurance, among others. When the patient personal information icon on the data file menu is selected by a user, other than the user (e.g., treatment professional) creating the clinical data file, the patient profile section 454 can be as illustrated without the indicators, as discussed herein.

Each patient personal data information data field 456 can be associated with an indicator 458. Similarly to the indicators 358 of FIG. 3, the indicators 458 can be of any suitable type. In some embodiments, the indicator 458 can be a box, as shown in FIG. 4, where the box can be "checked" to enable the indicator 458.

In such embodiments, when an indicator 458 is enabled, instructions executable by the processor can hide the information associated with the enabled indicator 458 when the clinical data file is being viewed by a user, as discussed herein. For example, when the indicator 458 associated with the patient's name is enabled, the patient's name can be hidden, and the patient's initials can be displayed in the data file menu, as discussed herein.

In some embodiments, the information associated with the enabled indicator 458 can be shown by entering a pass code, as discussed herein. In addition, in various embodiments, the indicator 458 can be a drop-down menu, where a user can select either "hide information," "display information," or "secure information" for each patient personal information data field 456.

In some embodiments, when a user selects the patient personal information icon on the data file menu, the patient profile can be displayed (e.g., as shown in FIG. 4 without the indicators 458), and the data fields associated with enabled indicators 458 can be displayed with, for example, the message "confidential information." In addition, data fields that are left blank when the clinical data file is created can be absent from the patient profile section 454. By distinguishing between a data field containing confidential information and a data field that is blank, a treatment professional can determine whether it would be useful to obtain permission to view the confidential information, rather than obtain permission to view confidential information only to find the data field blank.

Figure 5:
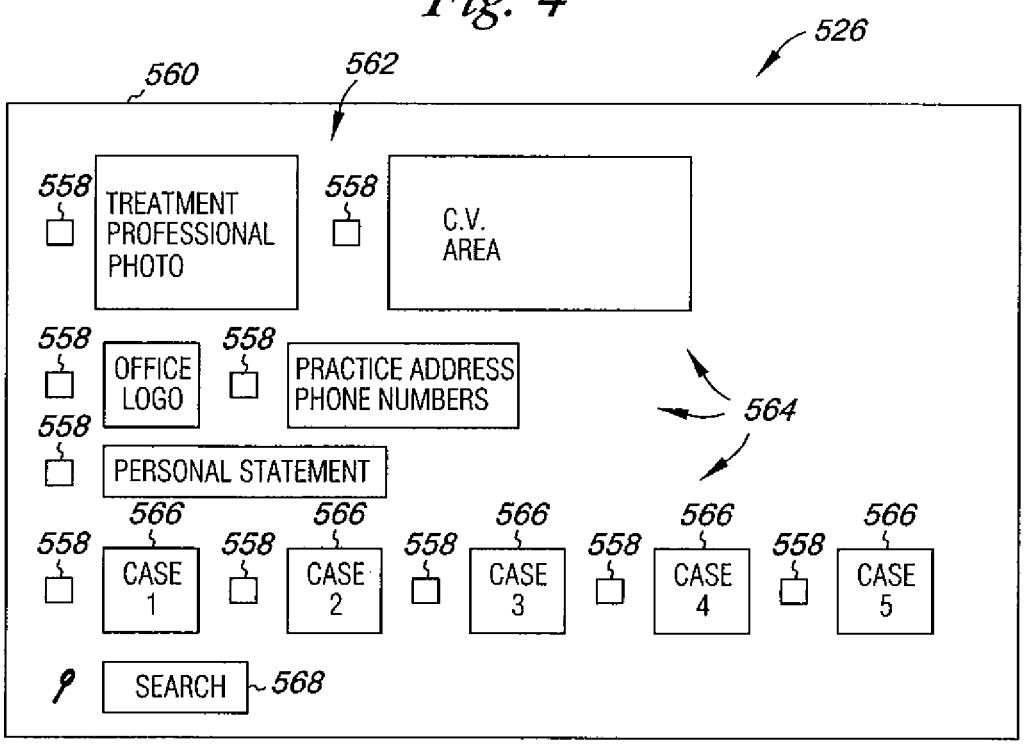
FIG. 5 is an illustration of a display of a treatment professional profile section according to an embodiment of the present disclosure.

FIG. 5 is an illustration of a display 526 of a treatment professional profile section 560 according to embodiments of the present disclosure. Similarly to the patient profile section (e.g., FIG. 4), the treatment professional profile section 560 illustrated shows the treatment professional profile section 560 when the clinical data file is created.

As discussed herein, when the treatment professional icon is selected, instructions can be executed by the processor to view the treatment professional profile section 560. The treatment professional profile section 562 can include various treatment professional data fields 564 that can be filled in with different types of information including, for example, a treatment professional photograph, a practice address and phone number, an office logo, a personal statement, consulting rates, and/or resume highlights, among others.

In some embodiments, the treatment professional profile section 562 can include sample cases 566 for a potential patient to view. The potential patient can select a sample case 566, where instructions executable by the processor can display a data file menu (e.g., FIG. 3), and the potential patient can see "before" and "after" images of, for example, a patient's teeth. The potential patient can then determine if the treatment professional is a good match for the particular treatment that the potential patient requires based on the sample cases 566.

In such embodiments, the clinical data file can include multiple treatment professional profiles including several sample cases 566. In addition, in some embodiments, the treatment professional profile section 562 can include a search tool 568. In such embodiments, the potential patient can enter a search term into the search tool 568, and instructions executable by the processor can display treatment professional profile sections 562 that include the search term.

In some embodiments, the treatment professional profile section 562 can include a rating indicating how much experience the treatment professional has with a certain treatment option. For example, the rating can indicate how much experience the treatment professional has with using technologies from Align Technology, Inc.

In addition, as discussed herein, in some embodiments, the treatment professional profile section 562 can include a data field 564 where the treatment professional can enter consulting rates. This information can be useful for a potential patient when selecting a treatment professional and/or a treatment professional seeking a second opinion.

In addition, the treatment professional can keep identifying information about the patients in the sample cases 566 private by enabling the indicators 558 associated with patient personal information data fields in the patient profile section, as discussed herein. Each treatment professional data field 564 can be associated with an indicator 558, as discussed herein with regard to the patient profile section (e.g., FIG. 4). When an indicator 558 is enabled, instructions executable by the processor can hide the information associated with the enabled indicator 558 when the clinical data file is being viewed by a user, as discussed herein.

In some embodiments, the information associated with the enabled indicator 558 can be shown by entering a pass code, as discussed herein. In addition, in various embodiments, the indicator 558 can be a drop-down menu, where a user can select either "hide information," "display information," or "secure information" for each treatment professional information data field 564.

In various embodiments, treatment professional information entered into data fields 564 associated with a disabled indicator 558 can be embedded into the clinical data file. In such embodiments, the treatment professional information can be unmodifiable except by the treatment professional, for example, by entering a pass code.

In some embodiments, when a user selects the treatment professional icon is selected on the data file menu, the treatment professional profile can be displayed (e.g., as shown in FIG. 5 without the indicators 558), and the data fields associated with enabled indicators 558 can be displayed with, for example, the message "confidential information." In addition, data fields that are left blank when the clinical data file is created can be absent from the treatment professional profile section 562, as discussed herein.

As discussed herein, when viewing the data file menu (e.g., FIG. 3), one or more patient images can be shown as a thumbnail. In addition, the thumbnail can be selected and instructions can be executable by the processor to enlarge the patient image.

Figure 6:
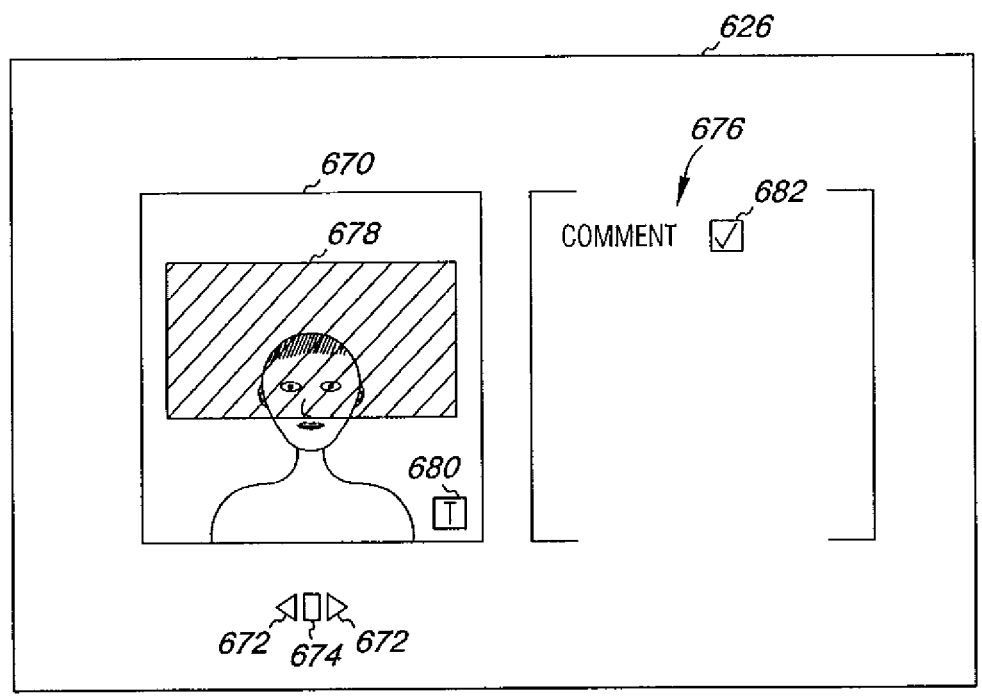
FIG. 6 is an illustration of a display of an enlarged patient image according to an embodiment of the present disclosure.

FIG. 6 is an illustration of a display 626 of an enlarged patient image 670 according to embodiments of the present disclosure. In some embodiments, the display 626 can include navigation arrows 672, where instructions can be executed by the processor to advance the enlarged patient image 670 from one image to the next patient image in the data file menu.

Instructions can also be executed to go back to the previous patient image in the data file menu when one of the navigation arrows 672 is selected. The display can also include a menu shortcut 674, where instructions can be executed by the processor to return to the data file menu (e.g., FIG. 3) when selected.

As illustrated in FIG. 6, the display of the enlarged patient image 670 can include a comments section 676 as discussed herein. In some embodiments, when the thumbnail of a patient image is selected, instructions can be executed by a processor to enlarge the patient image, as shown in FIG. 6, and to display comments associated with the patient image in the comment section 676.

In some embodiments, a patient image can include notations on the image. In some embodiments, a comment in the comment section 676 can explain the notation on the image.

In some embodiments, when the clinical data file is created and the patient images are imported, a user (e.g., treatment professional) can modify the patient image in various manners. For example, in some embodiments, modification can be accomplished by highlighting an area, by circling an aspect and/or area, and/or by including a privacy region 678. Such actions can be accomplished by executable instructions to perform and display such modifications.

FIG. 6 illustrates the privacy region 678 where an area of the enlarged patient image 670 is blacked out. Blacking out an area of a patient image can help a treatment professional hide identifying characteristics of a patient.

In some embodiments, the privacy region 678 can include an area of the patient image that is, for example, blurred rather than blacked out. In some embodiments, the privacy region 678 can be accessible by entering a pass code.

Including the privacy region 678 can allow a treatment professional to provide the clinical data file to a potential patient or to send the clinical data file to a second treatment professional for a second opinion without losing doctor-patient confidentiality. It can also allow the treatment professional to send the clinical data file over an unsecured internet connection (e.g., public email) while retaining the anonymity of the patient information included in the clinical data file. Including the privacy region 678 can also decrease the need for additional documentation between the treatment professional, patient, and second treatment professional regarding permission to view the clinical data file. In some embodiments, the user can include a comment in the comment section 452 explaining the modification and/or privacy region 678.

In some embodiments, the data file menu comment section (e.g., comment section 350 in FIG. 3) can include a list of comments such as comments regarding modifications to images and comments made by a treatment professional when creating and/or viewing the clinical data file, as discussed herein. In some embodiments, the comment section illustrated in FIG. 6 can include the list of comments displayed in the comment section on the data file menu.

In various embodiments, the comment section illustrated in FIG. 6 can include just the one or more comments associated with the enlarged patient image 670, as discussed herein. In some embodiments, the user can choose between viewing the entire list of comments from the data file menu or the comments associated with the enlarged patient image 670, or can select comments to be viewed.

As shown in FIG. 6, the enlarged patient image 670 can include a toolbar 680 for modifying the enlarged patient image 670. When the toolbar 680 is selected, instructions executed by the processor can cause tools to appear, such as, text tools, fill tools, and/or draw tools, including circle, square, pen size selection, and/or color selection, among others.

An exit tool can also appear when the toolbar 680 is selected, in some embodiments. In such embodiments, once the tools appear, a user can modify the enlarged patient image 670 to highlight an area of interest and/or to make a notation on the enlarged patient image 670, among other modifications.

Once the user is finished, the user can select the exit tool and instructions executable by the processor can save the modifications. In addition, the user can enter comments into the comment section 676, as discussed herein, explaining the modifications and/or inquiring about a portion of the enlarged patient image 670.

Other types of comments can also be entered into the comment section 676. For example, in some embodiments, instructions executable by the processor can save the modifications and/or the comments entered into the comment section 676 separate from the enlarged patient image 670. In addition, by entering comments into the comment section 676 with the enlarged patient image 670, instructions executed by the processor can associate the comments with the enlarged patient image 670 displayed when the one or more comments are entered.

As discussed herein, in some embodiments, the comments entered into the comment section 676 with the enlarged patient image 670 can also be seen on the data file menu in the comment section as a discussion thread. In embodiments where the comments entered are associated with the enlarged patient image 670 displayed when the comment is entered, a tag 682 can be inserted into the comment section 676 with the enlarged patient image 670 as well as next to the comment in the comment section on the data file menu.

As used herein, the tag 682 refers to an icon, where the icon can be a graphic picture (e.g., a pencil), and/or a textual hyperlink. In such embodiments, instructions can be executed by a processor to enlarge the modified patient image associated with the comment when the tag 682 is selected. In some embodiments, more than one modified patient image can be enlarged when multiple tags 682 are selected.

As discussed herein, in some embodiments, a treatment professional can send the clinical data file to a second treatment professional for a second opinion. In some embodiments, the second treatment professional can modify the enlarged patient images 670 and/or insert comments.

In such embodiments, by associating a tag with a comment when the comment is inserted after the enlarged patient image 670 is modified, the treatment professional can view the enlarged patient images 670 directly from the data file menu by selecting the tag 682 associated with the comment. This can help the treatment professional follow the order in which the second treatment professional viewed the clinical data file, facilitating greater understanding of the second opinion and the thought process to form the second opinion.

In some embodiments, once the user is finished modifying the enlarged patient image 670 and/or entering comments into the comment section 676 and selects the exit tool, instructions can be executed by the processor to secure the comments and/or modifications from further modification. In some embodiments, the comments and/or modifications can be modified after entering a pass code into the computing device.

In some embodiments, instructions are executed by the processor to send the clinical data file to a second computing device. In various embodiments, the clinical data file can be sent to a second user, as discussed herein, where the user can view the clinical data file on the same computing device, a second computing device, or an unnetworked computing device by transport of one or more files on a portable computing device readable medium.

For example, the clinical data file can be sent from a first treatment professional to a second treatment professional via the Internet. The second treatment professional can then open and view the clinical data file on a display at any computing device that includes a computing device readable medium having instructions which can be executed by a processor to cause a computing device to view the clinical data file.

In some embodiments, once the clinical data file is received, instructions which can be executed by a processor can cause the computing device to view the clinical data file menu (e.g., as shown in FIG. 3), on a display 626. The clinical data file menu can include, for example, one or more thumbnails of patient images, one or more tabs in a sequence of tabs, one or more comment sections, patient personal information, and/or treatment professional information, as discussed herein. In addition, a thumbnail can be selected to enlarge the patient image.

In such embodiments, the treatment professional or other user who receives the clinical data file can use the tool bar 680 to modify one or more enlarged patient images 670, and/or can enter comments into the comment section 676. As discussed herein, a tag 682 can be inserted in the comment section 676 when the comment is associated with the enlarged patient image 670 that is modified and/or that is displayed when the comment is entered. The treatment professional or other user can repeat this process for as many patient images as desired.

As discussed herein, the modifications and comments can be saved separately from the enlarged patient images 670. In such embodiments, the treatment professional, or other user, can send the modifications and comments to the computing device that the clinical data file was received from and/or to another computing device or save to a fixed or portable computing device readable medium. When the original computing device and/or different computing device receives the modifications and/or comments, instructions can be executed by the processor to allow the receiving user to accept or reject the modifications and/or comments.

In embodiments where the receiving computing device includes the clinical data file, accepting the modifications and/or comments can cause instructions executed by the processor to save the modifications and/or comments and merge them with the clinical data file. In embodiments where the receiving computing device does not include the clinical data file, accepting the modifications and/or comments can cause instructions executed by the processor to save the modifications and/or comments as well as the entire clinical data file. In some embodiments, the user sending the modifications and/or comments can choose whether to send the modifications, comments, and/or the entire clinical data file.

By saving the modifications and/or comments separately from the enlarged patient images 670, the enlarged patient image 670 as well as the clinical data file can be maintained in the form in which it was created. This can help to prevent unintended and/or unauthorized modifications to the clinical data file.

Allowing the user to accept or reject modifications and/or comments can also help to prevent unauthorized modifications. In addition, saving the modifications and/or comments separately from the enlarged patient images 670 can preserve the original, unaltered patient image, which may be important for medico-legal documentation purposes.

In some embodiments, the modifications and/or comments can be saved separately from the enlarged patient images 670 and arranged as layers on the enlarged patient images 670. In such embodiments, the layers of modifications can be removed (e.g., by entering one or more pass codes) to revert to the original, unaltered patient image and other information. In other words, the enlarged patient images 670 and modifications and/or comments can be viewed separately, in some cases, by entering a pass code.

In some embodiments, more than one treatment professional, or other user, can send modifications and/or comments to the original treatment professional. In such embodiments, when the modifications and/or comments are accepted, instructions executed by the processor can cause more than one set of modifications and/or comments to be merged with the clinical data file.

In such embodiments, the different sets of modifications and/or comments can be displayed with an identifier to indicate the sender. For example, each treatment professional, or other user, sending modifications and/or comments can be assigned a different color, identifier, and/or font.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method comprising:
    obtaining an original patient data file comprising:
        one or more patient personal information data fields comprising patient personal information of a patient to be treated for a dental condition with a treatment plan, and
        patient medical information items comprising: one or more patient images representing the patient at one or more stages of the treatment plan;
    processing computer-program instructions to designate a selected portion of the one or more patient images in the original patient data file as private;
    creating one or more anonymized patient images comprising the one or more patient images having a privacy region over the selected portion of the one or more patient images;
    displaying, via a user interface, the one or more anonymized patient images alongside at least a part of the patient personal information;
    processing computer-program instructions to modify the one or more anonymized patient images with one or more notations;
    associating the privacy region and the one or more notations with the patient personal information in the original patient data file to provide a first updated patient data file; and
    displaying the one or more modified anonymized patient images with the privacy region and the one or more notations as one or more layers on the one or more patient images, wherein the one or more layers is removable by entering one or more pass codes.

2. The method of claim 1, wherein the privacy region comprises a blurred region to opacify the at least a portion of the one or more patient images.

3. The method of claim 1, wherein the privacy region comprises a blacked-out region to obscure the at least a portion of the one or more patient images.

4. The method of claim 1, wherein the one or more anonymized patient images comprise one or more enlarged patient images having the privacy region placed thereon.

5. The method of claim 1, further comprising securing the one or more notations from edits using a password associated with the original patient data file.

6. The method of claim 1, further comprising:
    receiving the one or more pass codes associated with the original patient data file; and
    removing the privacy region from the one or more anonymized patient images in response to the password one or more pass codes.

7. The method of claim 1, wherein the instructions to designate the selected portion of the one or more patient images as private and the instructions to modify the one or more anonymized patient images are received from a first treatment professional.

8. The method of claim 1, wherein the instructions to designate the selected portion of the one or more patient images as private are received in response to a selection from a user interface element on a display.

9. The method of claim 1, further comprising providing the first updated patient data file from a first treatment professional to a second treatment professional.

10. The method of claim 1, further comprising electronically mailing the first updated patient data file from a first treatment professional to a second treatment professional.

11. The method of claim 1, further comprising:
    providing the first updated patient data file from a first treatment professional to a second treatment professional;
    receiving, from the second treatment professional, a second input or a second modification to the one or more anonymized patient images related to the treatment plan;
    associating the second modification with the patient personal information in the first updated patient data file to provide a second updated patient data file, wherein the second modification is displayed as a second removable layer on the one or more anonymized patient images.

12. The method of claim 1,
    wherein the first updated patient data file comprises one or more tags associated with implementation of the treatment plan; and
    the method further comprises:
        providing the first updated patient data file from a first treatment professional to a second treatment professional;
        receiving, from the second treatment professional selection of the one or more tags; and
        associating data related to selection of the one or more tags with the patient personal information in the first updated patient data file to provide a second updated patient data file.

13. The method of claim 1, wherein displaying the one or more anonymized patient images comprises displaying an image gallery of thumbnails of anonymized patient images.

14. The method of claim 1, wherein:
    the original patient data file comprises treatment professional information items comprising treatment professional information; and wherein displaying the one or more modified anonymized patient images comprises displaying at least a portion of the treatment professional information.

15. The method of claim 1, wherein the one or more patient images comprise one or more of: facial anterior repose images; one or more facial anterior smiling images; one or more profile repose images; one or more profile smiling images; one or more right buccal images; one or more left buccal images; one or more anterior intraoral images; one or more upper occlusal images; one or more lower occlusal images; one or more close-up smile images; one or more individual teeth images; one or more patient medical history images; one or more dental 2D history images; one or more patient diagnosis images; one or more three-dimensional (3-D) model of a patient's mouth; one or more full mouth series x-rays; one or more panoramic x-rays; one or more cephalometric x-rays; and one or more and individual radiographs.

16. The method of claim 1, wherein the privacy region is saved separately from the one or more patient images.

17. The method of claim 1, wherein the one or more notations is saved separately from the one or more patient images.

18. The method of claim 1, further comprising sending the first updated patient data file to a second treatment professional via the internet.

19. The method of claim 1, further comprising generating a data file menu on the user interface, the data file menu comprising one or more indicators that enable a user to designate at least a portion of the one or more patient images as private.

20. The method of claim 1, wherein the one or more pass codes includes an identifier associated with a computing device or network.

21. The method of claim 1, further comprising saving the one or more layers separately from the one or more patient images.

22. The method of claim 1, wherein the privacy region is not over the patient's teeth such that the one or more anonymized patient images shows the patient's teeth.

23. A system comprising:
memory comprising computer-program instructions;
one or more processors coupled to the memory and configured to use the computer-program instructions on the memory to execute a method comprising:
  obtaining an original patient data file comprising:
    one or more patient personal information data fields comprising patient personal information of a patient to be treated for a dental condition with a treatment plan, and
    patient medical information items comprising: one or more patient images representing the patient at one or more stages of the treatment plan;
  processing computer-program instructions to designate a selected portion of the one or more patient images in the original patient data file as private;
  creating one or more anonymized patient images, the one or more anonymized patient images comprising the one or more patient images having a privacy region over the selected portion of the one or more patient images;
  displaying the one or more anonymized patient images alongside at least a part of the patient personal information in a display;
  processing computer-program instructions to modify the one or more anonymized patient images with one or more notations;
  associating the privacy region and the one or more notations with the patient personal information in the original patient data file to provide a first updated patient data file; and
  displaying as the one or more modified anonymized patient images with the privacy region and the one or more notations as one or more layers on the one or more patient images, wherein the one or more layers is removable by entering one or more pass codes.

24. The system of claim 23, wherein the privacy region is saved separately from the one or more patient images.

25. The system of claim 23, wherein the one or more patient images includes one or more photographs, x-rays and 3D models.

* * * * *